United States Patent [19]

Semerak et al.

[11] Patent Number: 4,916,956
[45] Date of Patent: Apr. 17, 1990

[54] CATALYST SAMPLING DEVICE

[75] Inventors: Henry J. Semerak, Sarnia; Lawrence M. Schmidt; Graham J. Griffiths, both of Clearwater, all of Canada

[73] Assignee: Polysar Limited, Sarnia, Canada

[21] Appl. No.: 325,960

[22] Filed: Mar. 20, 1989

[51] Int. Cl.⁴ ............................................... G01N 1/00
[52] U.S. Cl. .................................... 73/863; 73/866.5
[58] Field of Search ................ 73/863, 863.81, 863.82, 73/863.85, 863.86, 866.5

[56] References Cited

U.S. PATENT DOCUMENTS

| | | | |
|---|---|---|---|
| 3,162,049 | 12/1964 | Blanchard | 73/863.85 |
| 3,174,332 | 3/1965 | Echtler, Jr. et al. | 73/863.85 |
| 3,561,274 | 2/1971 | Haunschild | 73/863.86 |
| 3,786,682 | 1/1974 | Winter et al. | 73/863.86 |
| 3,973,440 | 8/1976 | Van de Ven et al. | 73/863.81 |
| 4,294,124 | 10/1981 | Kalwaitis | 73/863.85 |
| 4,631,961 | 12/1986 | Yohe et al. | 73/863.85 |
| 4,697,465 | 10/1987 | Evans | 73/866.5 |

Primary Examiner—Robert R. Raevis
Attorney, Agent, or Firm—Stevens, Davis, Miller & Mosher

[57] ABSTRACT

A system for exposing a sample to the interior of a reaction vessel has a pair of chambers interconnected by a passage. Each of the chambers may be isolated by valves with the outer chamber being removable. A sample holder is slidable between the chambers by a charging device and can be locked in place by rotation of the charging device. Flights on the interior of the passage provide guidance and facilitate locking.

21 Claims, 5 Drawing Sheets

4,916,956

CATALYST SAMPLING DEVICE

BACKGROUND OF THE INVENTION

The present invention relates to a system for exposing a sample to the interior of a reaction vessel.

In the chemical industry it is frequently necessary to monitor the conditions within a reaction vessel to ensure optimum operating parameters. This may be done on the basis of experience and/or computer modeling of the reaction within the vessel but it is preferable to monitor the exact conditions existing within the vessel. One technique used for such determination is to expose a sample of the material being tested (catalyst, dessicant or the like) to the conditions within the vessel and determine from subsequent inspection of the sample the conditions within the reaction vessel. Such sampling needs to be conducted with minimum disturbance to the reaction vessel and without the need to shutdown the entire process. It is also frequently necessarY to maintain the sample within an inert atmosphere to obtain an accurate determination of conditions within the vessel.

Previous proposals for obtaining such samples include the use of a rod-seal valve, such as those sold under the trademark RAM-SEAL by Fetterolf Corporation of Pa., U.S.A. However, rod-seal valve systems are considered to be susceptible to mechanical difficulties when operated in an environment containing non-uniformly sized, abrasive catalyst particles. Furthermore, although such systems do provide for the withdrawal of samples from the reactor, they do not readily permit the insertion of an isolated sample into the reactor.

It is therefore an object to the present invention to obviate or mitigate the above disadvantages.

SUMMARY OF THE INVENTION

The present invention in general terms comprises of a system for exposing a sample to the interior of a reaction vessel which comprises a first chamber within the reaction vessel and a second chamber outside the reaction vessel. A conduit interconnects the two chambers and a sample holder is moveable within the conduit between the two chambers. A device is used to move the holder between the two chambers. Each of the chambers may be sealed by closure devices and the second chamber is removable from the reaction vessel so that the sample holder may be removed within an inert atmosphere provided within the chamber for further inspection.

It is preferred that locking devices are provided to hold the holders in either of the chambers and that these locking devices are operated by the device that accomplishes movement of the sample holder between the two chambers.

In this manner it is possible to expose the sample to the interior of the reaction vessel with minimum disturbance to the reaction vessel itself and to subsequently remove the holder from the vessel within its inert atmosphere for subsequent evaluation.

BRIEF DESCRIPTION OF THE DRAWINGS

An embodiment to the invention will now be described by way of example only with reference to the accompanying drawings in which.

DETAILED DESCRIPTION

Figure 1:
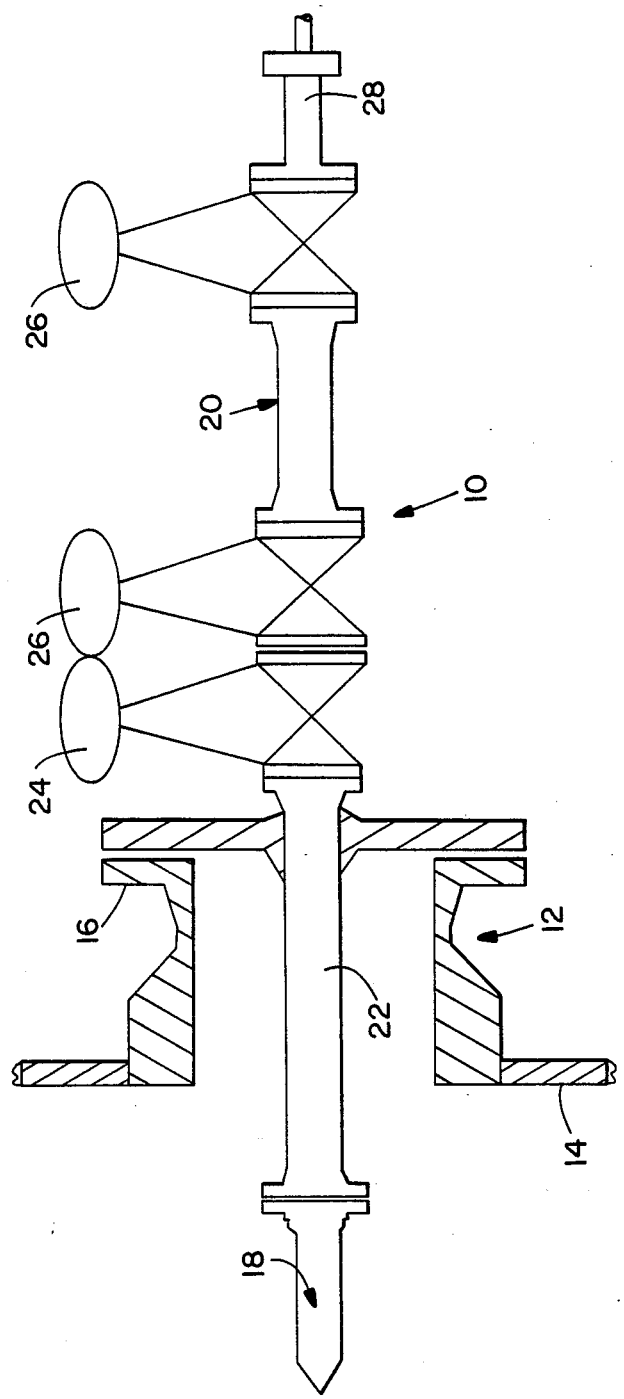
FIG. 1 is a schematic representation of the system installed on a reaction vessel.

Referring to FIG. 1, a sampling system 10 is connected to the inspection port 12 of a reaction vessel 14 by means of a flange 16 and so extends from the exterior to the interior of the vessel 14. The system 10 comprises a first chamber indicated at 18 located on the interior of the vessel 14, a second chamber indicated at 20 located on the exterior of the vessel 14 and a passage 22 interconnecting the chambers 18 and 20. The chamber 18 may be sealed by means of a valve 24 secured to the outer end of the passage 22 and the chamber 20 may be isolated by means of a pair of valves 26 located at opposite ends of the chamber 20. A charging device 2B is detachably secured to the outer valve 26 and is used for moving a sample holder 30 shown in detail in FIG. 3 between the chambers 18 and 20.

Figure 2:
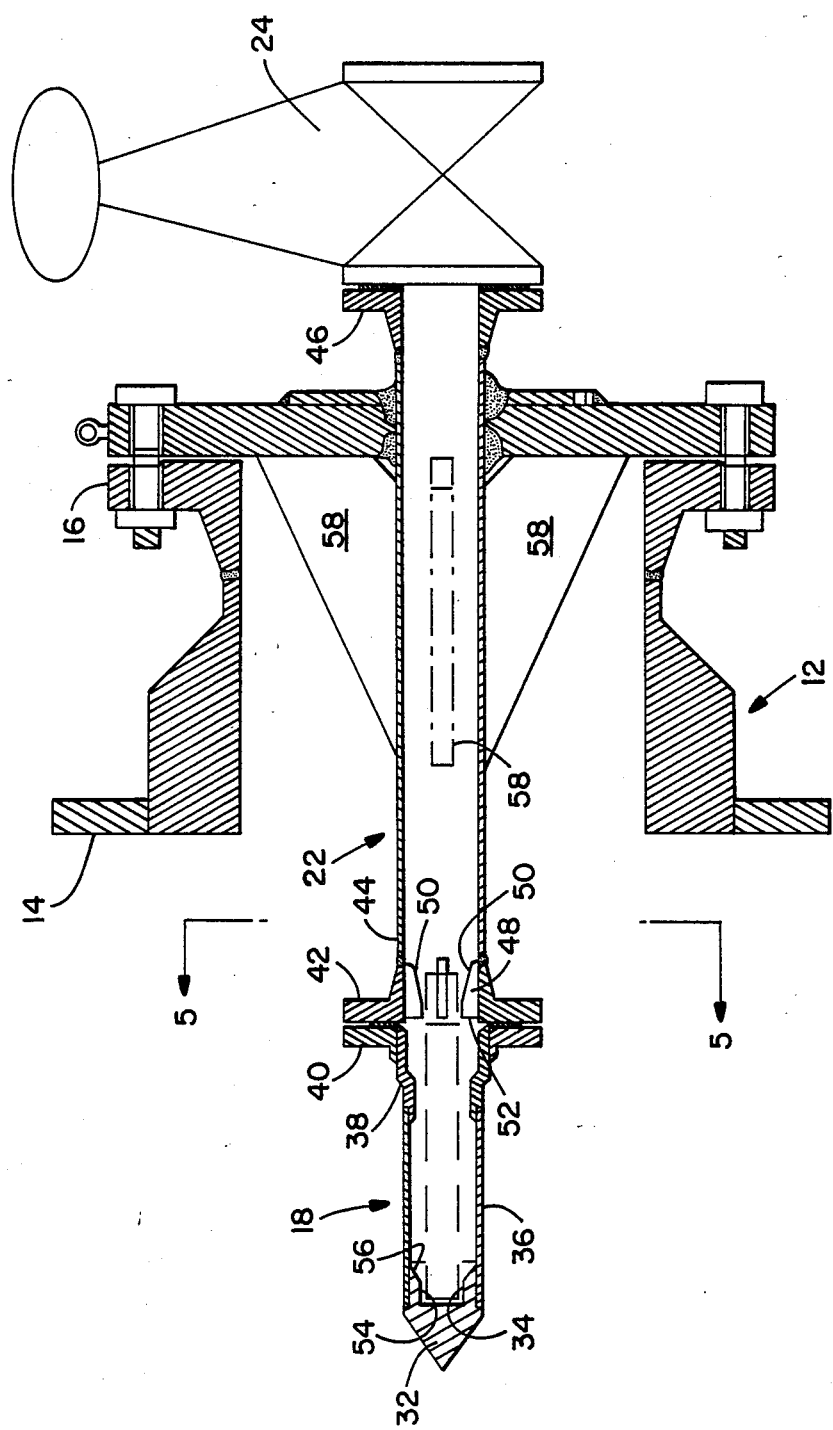
FIG. 2 is a enlarged sectional view of a portion of the system shown in FIG. 1.

The chamber 18 and passage 22 is shown in further detail in FIG. 2. Chamber 18 comprises an end cap 32 that is counterbored and flared as indicated at 54,56 respectively. The outer surface of end cap 32 has a recess 34 to receive a perforated outer screen 36 that forms the side wall of chamber 18. The opposite end of the screen 36 is secured to a boss 38 which in turn is connected to a flange 40. The flange 40 mates with corresponding flange 42 secured to a tube 44 that extends through the flange 16 from the outside to the inside of the vessel 14 and is supported on flange 16 by triangular webs 58.

The outer end of tube 44 terminates in a flange 46 that is secured to the valve 24 in a conventional manner. Valve 24 is also of conventional construction having a continuous axial passage when the valve is open of at least the same diameter as the internal diameter of tube 44. Valve 24 when closed seals the tube 44 to prevent communication across the walls of the reaction vessel 14.

Figure 6:
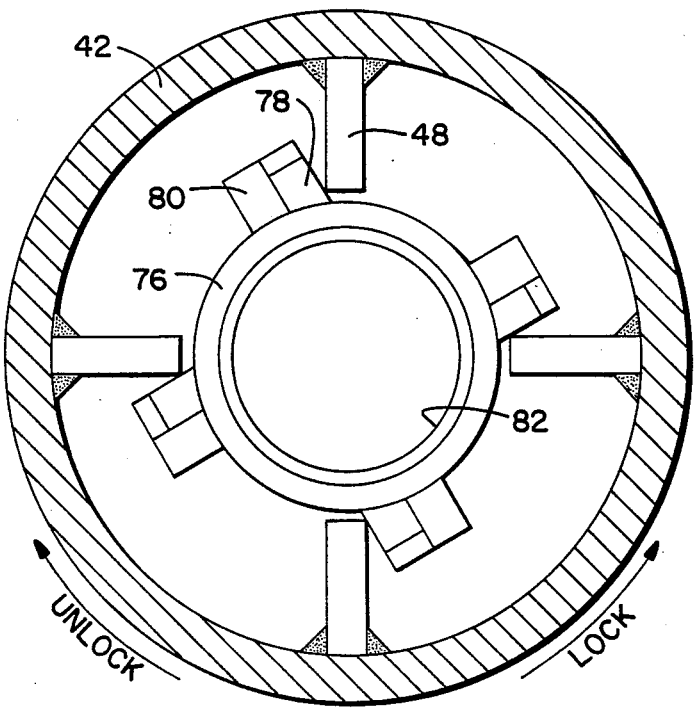
FIG. 6 is a view similar to FIG. 5 with the sample holder in an alternative position.

Located within the flange 42 are a plurality of flights 48. As can best be seen in FIG. 6, each of the flights extends radially inwardly from the interior of flange 42 and are spaced at 90 degree intervals around the circumference of the flange 42. Each of the flights 48 includes a tapered surface 50 leading to a radial surface 52 disposed toward the end cap 32.

Figure 3:
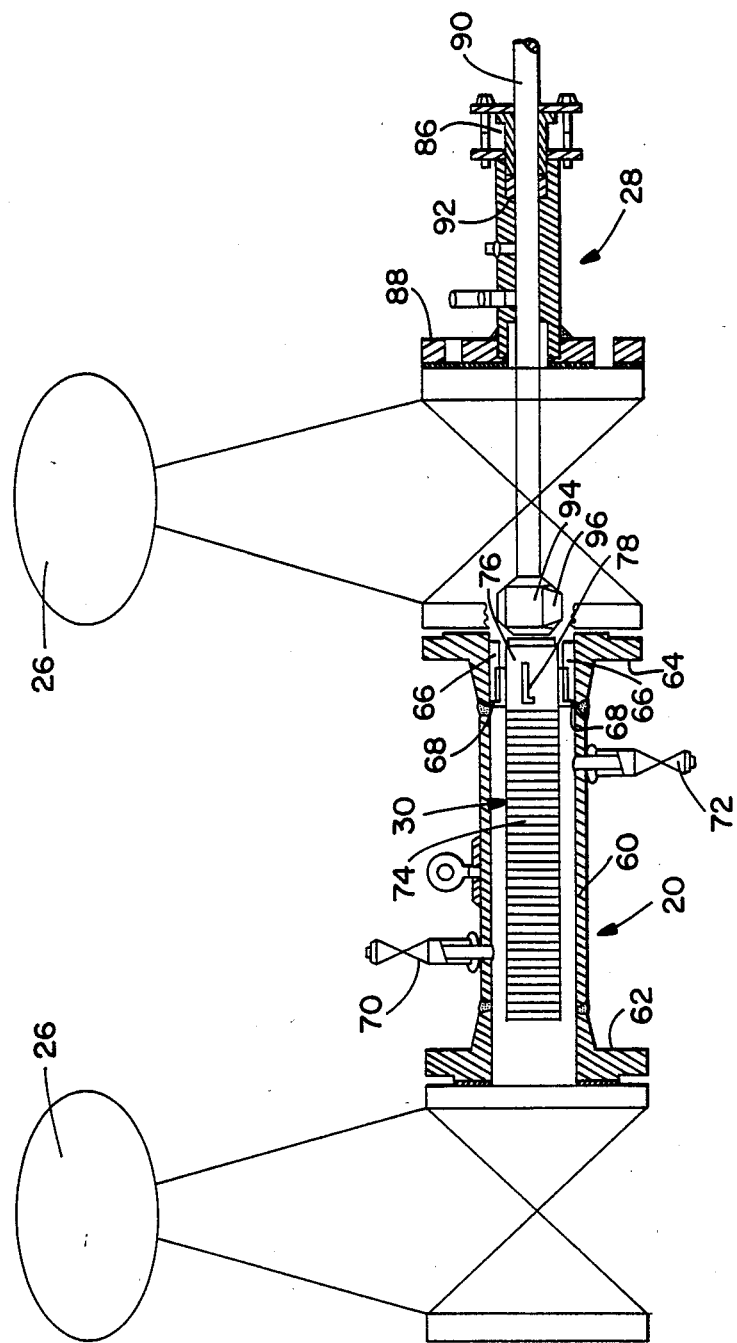
FIG. 3 is a sectional view on enlarged scale of the balance of the system shown in FIG. 1.

The details of the chamber 20 and charging device 28 are best seen from FIG. 3. The chamber 20 comprises a tubular body 60 having a flange member, 62 64 respectively, mounted at opposite ends. Flanges 62 and 64 are secured to the valves 26 in a conventional manner with the valves 26 also being of conventional construction providing a continuous passage corresponding to and aligned with the passage in the valve 24. Located within the body 60 on the interior surface of the flange 64 are a plurality of equally spaced flights 66 having a radially extending surface 68. Purging ports 70 and 72 are also provided on the body 60 to permit fluid (typically, an inert gas such as nitrogen) to b introduced into the 20.

Supported within the chamber 20 is a sample holder 30 comprising a cylindrical, screened body 74 which encloses the sample. The sample holder 30 is attached to a cylindrical plinth 76 by appropriate fastening means such as a welded seam. The mesh size of the screen of sample holder 30 is selected so as to prevent the loss of sample from the sample holder 30 into the reaction vessel. The plinth 76 is formed with radially extending flights 78 equally disposed around the periphery of the plinth 76 and corresponding in number to the flights 66. Each of the flights 78 includes a circumferentially extending leg 80 for engagement with the radial surface 68 of the flight 66.

Figure 4:
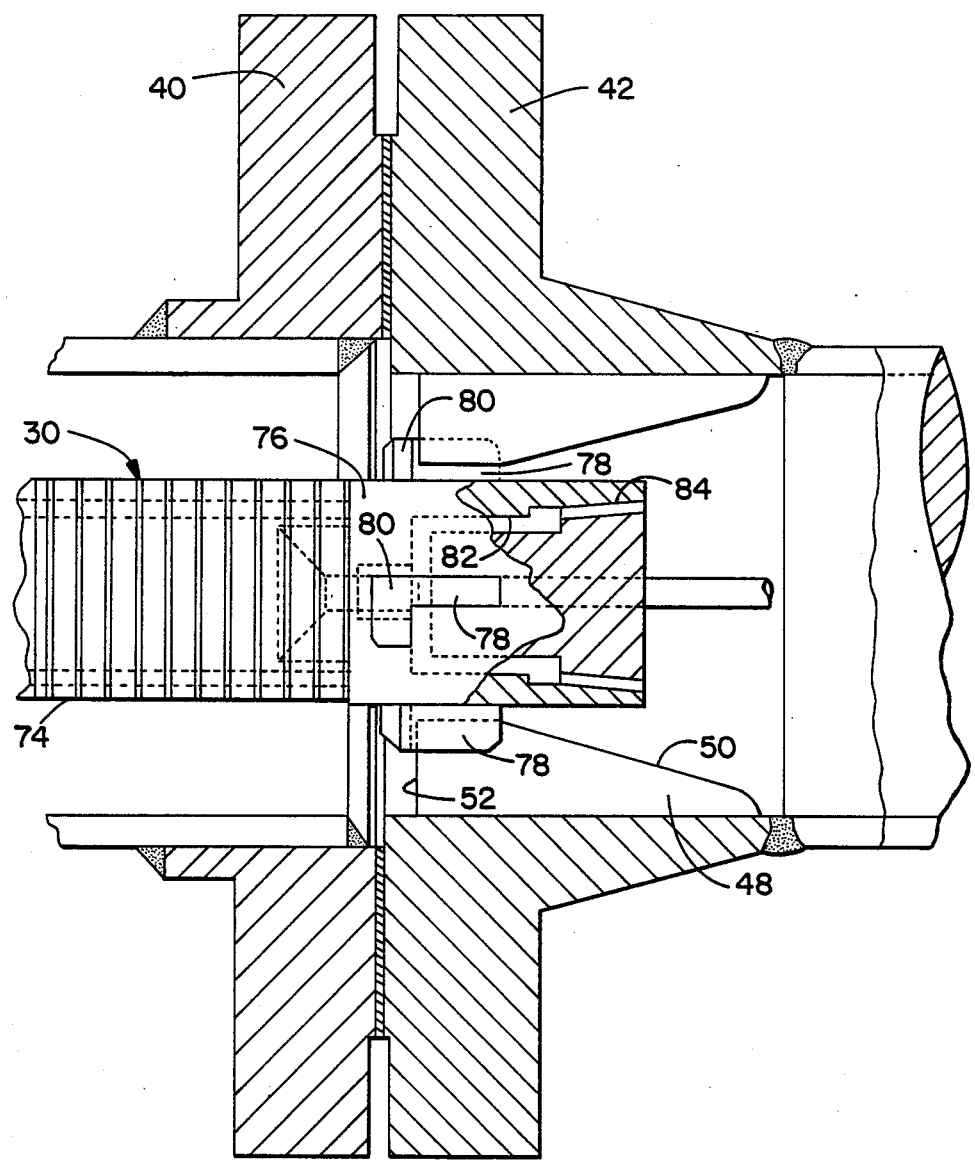
FIG. 4 is a detail of the device shown in FIG. 2 with the sample holder in a alternative position.

As can best be seen in FIG. 4, the plinth 76 is counterbored as indicated at 82 and threaded as indicated at 84.

Referring once again to FIG. 3, the charging device 28 comprises a stuffing box 86 secured to valve 26 by a flange 88. A rod 90 passes through the stuffing box 86 with a seal 92 disposed about the shaft 90. An enlarged boss 94 is secured to one end of the rod 90 and has a plurality of radially extending flights 96 circumferentially spaced around the surface of the boss 94. The distal end of the boss 94 is threaded (not shown). Referring back to FIG. 4, the threaded distal end of the boss 94 (not shown) cooperates with the threads 84 in the vicinity of the counterbored section 82 of the plinth 76. Thus, the boss 94 can be detachably attached to the plinth 76 via the plinth threads 84 and the cooperating threads on the distal end of the boss 94.

The operation of the sampling system will now be described assuming that the chamber 20 and charging device 28 are disassembled from the vessel 14. The sample holder 30 is first inserted into the chamber 20 by attaching the sample holder to the boss 94 of the charging device 28. The valve 26 is opened and the sample holder 30 inserted into the interior of the chamber 20. The flange 88 is secured to the valve 26 and the rod 90 advanced through the stuffing box 86 to move the flight 78 past the flights 66. The circumferential spacing of the two sets of the flights permits them to pass one another for movement into the chamber 20. With the sample holder located in the chamber 20, the rod 90 is rotated counter-clockwise to bring the legs 80 into a position overlying the radial face 68 of flights 66. This is facilitated by abuttment between the flights 66 and flights 78 that inhibits further rotation of the sample holder 30. The legs 80 serve to inhibit axial movement of the holder 30 out of the chamber 20 towards the charging device 28.

The chamber 20 and charging device 28 are then mounted as a unit on the valve 24. The valve 24 is opened providing a passageway from the chamber 20 into the chamber 18. The rod 90 is advanced to move the sample holder 30 through the valves 26, 24 and the tube 44 into the chamber 18. During this movement, the flights 96 on the boss 94 served to maintain the sample holder 30 centrally within the tube 44 with the flights 96 also being configured to pass through the flights 66.

As the sample holder 30 approaches the chamber 18, the tapered surface 50 on the flights 48 further centralizes the sample holder 30 and guides the sample holder into the chamber 18. Similarly the flared entrance to the counterbore 54 serves to locate the sample holder 30 within the counterbore 54 so it is supported at one end by the counterbore 54 and at its opposite end by the flights 48. With the sample holder 30 located within the chamber 18, it is locked by rotation of the rod 90 in a counter-clockwise direction. This rotation brings the flights 78 into abutment with the flights 48 with the leg 80 overlapping the radial face 52. The sample holder 30 is thus firmly secured against axial movement from within the chamber 18. The sample holder is then released from the charging device 28 by continued rotation of the rod 90 which undoes the threads 98 and 84. The abutment of the flights 78 with the flights 48 prevents continued rotation of the sample holder to facilitate the release.

The rod 90 may then be withdrawn and the valve 24 closed to seal the first chamber within the vessel 14. Similarly the chamber 20 and charging device 28 maybe disconnected through the valve 26 until such time as the sample has been exposed for the desired time to the conditions within the vessel. The screen 36 ensures communication between the sample holder and the interior of vessel 14 so that the sample may be subjected to the operating conditions within the vessel 14. It will also be noted that the insertion of the sample can be accomplished with the vessel in operation by virtue of the sealed environment provided by the seal 92 around the shaft 90.

Figure 5:
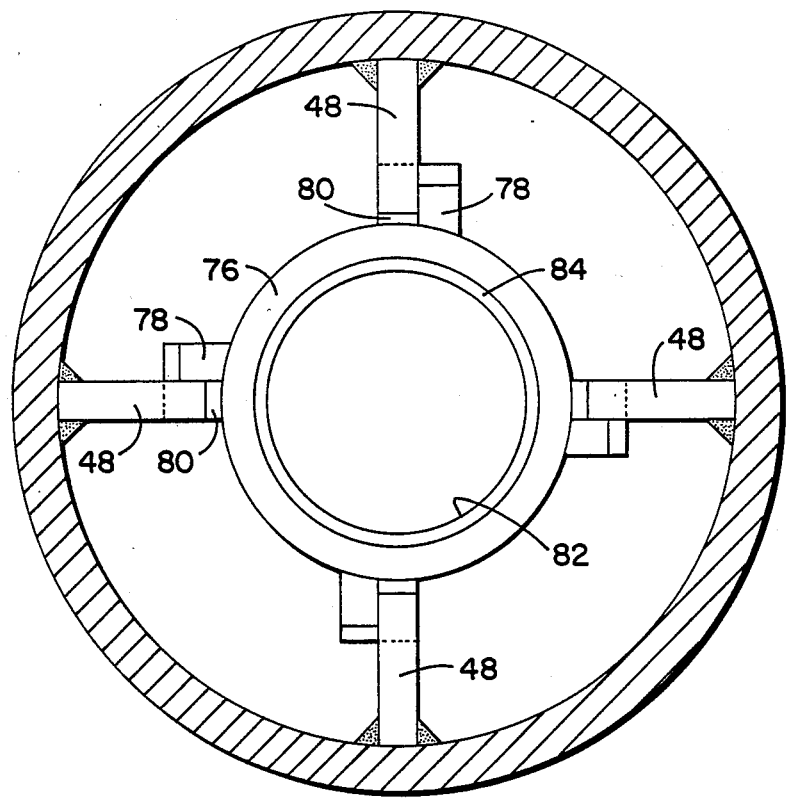
FIG. 5 is a view 5—5 FIG. 2.

In order to collect the sample from within the vessel 14, the chamber 20 and charging device 28 are once again connected to the valve 24. The valve 24 is opened the rod 90 to be advanced into the interior of the vessel 14. The flights 96 once again support the rod as it passes between the chambers and ensures engagement of the threads 98 with the threads 84 on the sample collector. Clockwise rotation of the rod will attach the sample holder 30 to the boss 94. Once the threads are fully engaged, continued rotation will move the sample holder 30 from the position shown in FIG. 5 in which the legs 80 overlie the radial surfaces 52 to the position shown in FIG. 6 in which the legs 80 are free from the flights 48. This permits the rod to be withdrawn and bring with it the sample holder 30. The rod is withdrawn until the sample holder 30 is located within the chamber 20. Valve 24 is then enclosed as is valve 26 to seal one end of the chamber 20. The sample holder is then located through manipulation of the rod 90 so that the flights 66 and 78 engage with the legs 80 overlying the radial face 68. In this position the rod may be rotated counterclockwise to release the threads 84 and allow the rod to be withdrawn into the stuffing box 86 beyond the valve 26. Valve 26 may then be closed to isolate the chamber 20 and if necessary the chamber 20 purged with a desired fluid, such as introgen, through the ports 70, 72. The charging device 28 may be removed through detachment at the flange 88 from valve 26 and detachment of the valve 26 from the valve 24. The sample holder is secured within the chamber which may be removed for further inspection at a appropriate location.

The present system is well suited for testing the catalyst used in a process to selectively hydrogenate the acetylenes contained in a butadiene-rich hydrocarbon stream.

It will be seen therefore that the system described above provides simple yet effective installation and removal of a sample holder from within a reaction vessel and provides for collection of the sample holder within an inert atmosphere if necessary. The sample holder is securely located at all stages of its travel with insertion and removal being accomplished without disturbance of the vessel 14 itself. The simple locking mechanism described is operable through the charging device to maintain simplicity and full operation of the system.

What is claimed is:

1. A system for exposing a sample to the interior of a reaction vessel comprising a first chamber located within said reaction vessel, a second chamber located outside said reaction vessel, a conduit interconnecting said chambers, a sample holder movable within said conduit between said chambers, moving means to move said holder between said chambers, first closure means to seal said first chamber from said second chamber, and second closure means to isolate said second chamber and permit detachment thereof from said reaction vessel, characterized in that said moving means are detachable from said holder when said holder is located within said first chamber.

2. A system according to claim 1 including lock means operable between said holder and said first chamber to inhibit movement within said first chamber.

3. A system according to claim 2 wherein said lock means is operable by said moving means.

4. A system according to claim 3 wherein said lock means includes interengaging formations on said holder and said chambers.

5. A system according to claim 4 wherein said interengaging movements are moved into and out of engagement by said moving means.

6. A system according to claim 5 wherein said moving means are attachable to said holder and said lock means are operable to inhibit movement of said holder and facilitate attachment of said moving means thereto.

7. A system according to claim 6 wherein said lock means are operable by rotation of said holder about the axis of said conduit.

8. A system according to claim 7 wherein said formations permit limited rotational movement between said holder and said first chamber and said moving means is threaded on to said holder.

9. A system according to claim 8 wherein said formations inhibit axial movement between said holder and said chamber when engaged.

10. A system according to claim 3 including support means to support said holder in said second chamber.

11. A system according to claim 10 wherein said support means inhibit axial movement of said holder.

12. A system according to claim 11 wherein said support means includes interengaging formations on said holder and second chamber respectively.

13. A system according to claim 12 wherein said formations are moved into engagement by said moving means.

14. A system according to claim 13 wherein said moving means are detachable from said holder and said support means are operable to inhibit movement of said holder.

15. A system according to claim 14 wherein said formations permit limited rotational movement between said holder and said second chamber and said moving means is threaded on said holder.

16. A system according to claim 14 wherein said moving means includes guides to direct said holder along said conduit between said first chamber and said second chamber.

17. A system according to claim 16 wherein said guides comprise flights secured to said moving means and configured to pass between the formations of said support means in said second chamber.

18. A system according to claim 17 wherein said moving means include an elongate rod slidable through said second chamber and along said conduit.

19. A system according to claim 18 including a seal member releasible secured to said second chamber and encompassing said rod to provide a seal there-between.

20. A system according to claim 2 including a guide member disposed at one end of said first chamber and cooperating with said lock means to support said holder in said first chamber.

21. A system according to claim 1 wherein said first chamber is perforated to communicate with the interior of said reaction vessel.

* * * * *